(12) United States Patent
Schwartz et al.

(10) Patent No.: US 9,944,982 B2
(45) Date of Patent: Apr. 17, 2018

(54) SURFACE CHEMISTRY AND DEPOSITION TECHNIQUES

(71) Applicants: Jerrod Schwartz, Stanford, CA (US); Stephen R. Quake, Stanford, CA (US); Milan Mrksich, Hinsdale, IL (US)

(72) Inventors: Jerrod Schwartz, Stanford, CA (US); Stephen R. Quake, Stanford, CA (US); Milan Mrksich, Hinsdale, IL (US)

(73) Assignees: STANFORD UNIVERSITY, Palo Alto, CA (US); UNIVERSITY OF CHICAGO, Chicago, IL (US); CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 14/092,728

(22) Filed: Nov. 27, 2013

(65) Prior Publication Data

US 2014/0256561 A1 Sep. 11, 2014

Related U.S. Application Data

(63) Continuation of application No. 12/024,584, filed on Feb. 1, 2008, now abandoned.

(60) Provisional application No. 60/899,173, filed on Feb. 2, 2007.

(51) Int. Cl.
*C12Q 1/68* (2018.01)
*G01N 33/543* (2006.01)

(52) U.S. Cl.
CPC ..... *C12Q 1/6874* (2013.01); *G01N 33/54353* (2013.01); *G01N 33/54393* (2013.01); *Y10T 436/143333* (2015.01)

(58) Field of Classification Search
CPC ........ C12C 1/68; C12C 1/6874; G01N 33/52; C40B 30/00
See application file for complete search history.

(56) References Cited

U.S. PATENT DOCUMENTS

| | | | |
|---|---|---|---|
| 5,629,213 A * | 5/1997 | Kornguth | B82Y 30/00 356/445 |
| 5,965,456 A | 10/1999 | Malmquist et al. | |
| 6,127,129 A | 10/2000 | Corn et al. | |
| 6,277,489 B1 | 8/2001 | Abott et al. | |
| 6,329,209 B1 | 12/2001 | Wagner et al. | |
| 6,787,308 B2 | 9/2004 | Balasubramanian et al. | |
| 6,956,651 B2 * | 10/2005 | Lackritz | G01N 21/253 356/445 |
| 2002/0164629 A1 | 11/2002 | Quake et al. | |
| 2005/0014175 A1 | 1/2005 | Quake | |
| 2005/0244863 A1 | 11/2005 | Mir | |
| 2006/0019276 A1 | 1/2006 | Harris et al. | |
| 2006/0024678 A1 | 2/2006 | Buzby | |
| 2006/0118754 A1 | 6/2006 | Lapen | |
| 2006/0228747 A1 | 10/2006 | Fuchs et al. | |
| 2007/0087382 A1 * | 4/2007 | Howorka | B01J 19/0046 435/7.1 |
| 2007/0099208 A1 | 5/2007 | Drmanac et al. | |

FOREIGN PATENT DOCUMENTS

WO   WO2005/025737   *   3/2005

OTHER PUBLICATIONS

U.S. Non-Final Office Action dated Nov. 1, 2012 for U.S. Appl. No. 12/024,584.
U.S. Non-Final Office Action dated Apr. 20, 2010 for U.S. Appl. No. 12/024,584.
International Search Report and Written Opinion from PCT application No. PCT/US08/52796 dated Jun. 27, 2008 (11 pages).
EP Supplementary European Search Report as dated Mar. 12, 2010 in EP application No. 08728823.9 (11 pages).
Communication pursuant to Article 94(3) EPC as issued on Nov. 8, 2011 in EP application No. 08728823.9 (8 pages).
Communication pursuant to Article 94(3) EPC as issued on Feb. 28, 2011 in EP application No. 08728823.9 (8 pages).
Kartalov et al, "Polyelectrolyte Surface Interface for Single-Molecule Fluorescence Studies of DNA Polymerase" Biotechniques, Informa Life Sciences Publishing, Westborough, MA, US. vol. 34, No. 3, Jan. 1, 2003 (Jan. 1, 2003), pp. 505-510, XP002310467, ISSN. 0736-6205 *introduction; p. 508* (4 pages).
Pammer Patrick et al., "Nanopatterning of biomolecules with microscale beads." Chemphyschem: A European Journal of Chemical Physics and Physical Chemistry May 2005, vol. 6, No. 5, May 2005 (May 2005), pp. 900-903, XP009129946, ISSN: 1439-4235 *figure 1; p. 903 last paragraph* (4 pages).
Smith et al., "Nanopatterning the chemospecific immobilization of cowpea mosaic virus capsid," 2003, Nano Letters, 3, 883-886.
Schwartz et al., "High Density Single Molecule Surface Patterning With Colloidal Epitaxy," Applied Physics Letters, American Institute of Physics; 91083902-1; downloaded Oct. 27, 2008.

* cited by examiner

Primary Examiner — Narayan Bhat
(74) Attorney, Agent, or Firm — Emily M. Haliday; Weaver Austin Villeneuve & Sampson LLP

(57) ABSTRACT

Surface chemistries for the visualization of labeled single molecules (analytes) with improved signal-to-noise properties are provided. To be observed, analyte molecules are bound to surface attachment features that are spaced apart on the surface such that when the analytes are labeled adjacent analytes are optically resolvable from each other. One way to express this concept is that binding elements should be spaced apart such that the Guassian point spread functions of adjacent labels do not overlap. Another way of expressing this concept is that the surface binding elements should be spaced apart by a distance equal to at least the diffraction limit for an optical label attached to the bound analytes.

16 Claims, 3 Drawing Sheets bis-biotin- 5' NNNNNNNNNNNNN $N_1N_1N_1N_1N_1$ NNNNN $n_2n_2n_2n_2n_2$ nnnnnnnn 3' - thiol-SMCC-Bead-
(SEQ ID NO:1)

3' NNNNNNNNNNNNN $N_1N_1N_1N_1N_1$ NNNNN $N_2N_2N_2N_2N_2$ nnnnnnnn 5' - $Cy^3$ (SEQ ID NO:2)

FIG. 1

~bis-biotin- 5' AAAAA (A)₆₀ AAAAA - cleavable linker-bead (SEQ ID NO:3)

1. cleavage of bead
2. anneal poly-T modified ssDNA

~bis-biotin- 5' AAAAA (A)₆₀ AAAAA 3' (SEQ ID NO:4)
             3' TTTTT (T)₆₀ TTTTT NNNNNNNNNNNNNNNNNNNN 5' (SEQ ID NO:5)

FIG. 3

SURFACE CHEMISTRY AND DEPOSITION TECHNIQUES

This application is a continuation of U.S. application Ser. No. 12/024,584, filed on Feb. 1, 2008, which claims priority to and benefit of U.S. Provisional Application Ser. No. 60/899,173, filed on Feb. 2, 2007, the entire content of which is incorporated herein by reference.

BACKGROUND OF THE INVENTION

In certain applications, such as single molecule DNA sequencing or the evaluation of polymerases, it is necessary to wash labeled biomolecules across a surface. This process inevitably results in the nonspecific binding of labeled molecules to the surface and a concomitant increased background fluorescence and false-positive features. Many surface attachment chemistries have intrinsic properties designed to enhance specific molecule binding but do little to directly inhibit or suppress the effects of the nonspecific binding of fluorescently labeled molecules. The corresponding increase in background fluorescence as labeled molecules are washed across the surface, combined with the limited fluorescent intensity and lifetime of any single fluorophore, imposes restrictions on the overall imaging capabilities of any single molecule surface chemistry. The spatial resolution of an optical system is limited by the Rayleigh criterion: $d_R = 0.61\lambda/N.A.$, where $\lambda$ is the wavelength of collected photons and N.A. is the numerical aperture of the system. As a result of these optical limitations, current methods for the surface deposition and visualization of fluorescently-labeled single molecules suffer from a number of fundamental limitations. Poisson statistics reveal that a certain fraction of all randomly distributed molecules on a surface will be located within a diffraction limit distance of at least one other molecule, resulting in neither of the two molecules being easily resolvable. As a result, for a given optical setup, as the number of deposited molecules increases, the total number of resolvable molecules reaches a maximum and then decreases. Recent a posteriori methods have been developed using centroid localization or photobleaching to resolve multiple single molecules within a diffraction-limited area with high precision. While some of these techniques could conceivably be used to increase the maximum number of resolvable molecules while using random deposition, they would require precise observation of every photobleaching event to realize a significant degree of accuracy. Given the sensitivity and capture rate limitations of current CCD technology, it would likely not be practical to use these methods to completely resolve a highly dense surface array of single molecules.

Common surface attachment chemistries, for both single molecule and bulk sample surface immobilization, typically involve specific ligand binding, specific covalent coupling, or nonspecific chemiabsorption or physiabsorption. Some examples include biotinstreptavidin or digoxygenin-antidigoxygenin coupling, azide-alkyne cycloaddition coupling (24), coupling between an amine-reactive substrate (eg. aromatic isothiocyanate) and a chemically modified aliphatic 1° amine biomolecule, or absorption to a positively charged poly-electrolyte surface followed by chemical or photochemical crosslinking. Many of these surface attachment chemistries have intrinsic properties designed to enhance specific molecule binding but some of them do little to inhibit the effects of nonspecific binding. However, the corresponding increase in background fluorescence as successive fluorescently labeled molecules are washed across the surface limits the overall imaging capabilities of any surface chemistry.

Various other chemical techniques have been developed to minimize background noise while optically imaging single molecules immobilized on a surface. These methods include using fluorescence resonance energy transfer (FRET) to resolve the relative proximity of molecules beyond the diffraction limit, building a negatively charged surface out of a polyelectrolyte multilayer to reduce nonspecific binding of fluorescently labeled nucleotides, using photo-cleavable or chemically cleavable fluorescent labels and extensive washing, and the use of a "smart" hydropolymer shield capable of preventing small molecule binding.

However, there remains a need in the art for a method of resolving single molecules on a surface, especially when random deposition of the molecules is desired.

SUMMARY OF THE INVENTION

The present invention provides surface chemistry for the visualization of labeled single molecules (analytes) with improved signal-to-noise properties. According to one aspect of the invention, analyte molecules to be observed are bound to surface attachment features that are spaced apart on the surface such that when the analytes are labeled adjacent analytes are optically resolvable from each other. One way to express this concept is that binding elements should be spaced apart such that the Guassian point spread functions of adjacent labels do not overlap. Another way of expressing this concept is that the surface binding elements should be spaced apart by a distance equal to at least the diffraction limit for an optical label attached to the bound analytes. For purposes of the invention, an analyte is any molecule that one wishes to observe. Preferred molecules are nucleic acids, proteins and other biomolecules.

The precise spacing of binding elements depends upon the label used. Diffraction limits of various optically-detectable labels are well known and can be selected at the convenience of the user. In one embodiment, a low-autofluorescence glass (e.g., a coverslip) is coated with a thin metal film and a specific surface coupling chemistry is applied for the attachment of labeled molecules. The metal film may be any appropriate metal (examples are provided below) at the convenience of the user and is applied such that total internal reflection illumination can be conducted on the surface. An evanescent field is generated by total internal reflection and is enhanced by the production of surface plasmons from the thin metal film, which increases the intensity of fluorescently labeled molecules within approximately 150 nm of the surface. This is explained by the fact that surface plasmons tend to stay longer along the surface than the evanescent field, and the electromagnetic field produced by the surface plasmons is intensified near the metal surface. The presence of the thin metal film quenches excited fluorophores near the surface (within tens of nm) by a mechanism of fluorescent energy transfer into the surface plasmon modes of the metal.

The invention also provides surface deposition methods that are useful independent of the surface chemistry being used. These deposition strategies allow for the fabrication of fully-resolved single molecule arrays at a feature density that surpasses that of any previously-described methods. Methods and devices of the invention improve the total resolvable molecule limit by selectively spacing deposited molecules at least a diffraction limit apart from every other molecule.

A particular application of methods and materials of the invention is for single molecule sequencing of nucleic acids. In particular, methods of the invention allow increased resolution of ordered arrays of nucleic acid duplex on surfaces for sequencing. In a preferred embodiment, primers for nucleic acid synthesis are placed on a surface as described herein. For ease of use, the primers can be universal primers, such as poly-T sequences. Genomic DNA (or RNA or cDNA copies of RNA) are then sheared and, in the case in which primers are poly-T, tailed with a polyadenylation sequence in order to hybridize to the primer (e.g., with a terminal transferase enzyme as is well-known in the art). After appropriate wash steps, labeled nucleotides are added in the presence of a polymerase enzyme for template-directed sequencing-by-synthesis. The resulting sequencing reactions allow visual observation of individual incorporated nucleotides in sequence. A general approach to single molecule sequencing is described in co-owned, U.S. Pat. No. 7,282,337, incorporated by reference herein.

Further aspects and features of the invention are provided below in the detailed description thereof.

DESCRIPTION OF THE DRAWINGS

FIG. 1 shows a sample DNA construct for diffraction limit spacing surface attachment. $N_1$=Type IIs restriction enzyme recognition site; $N_2$ and $n_2$=Type IIs restriction enzyme cut site. The fluorophore may alternatively be attached to the 3' end of the lower strand. Following cleavage, the dsDNA in lowercase letters is removed and washed away.

FIG. 3 shows a variant scheme for single molecule diffraction limit spacing with a universal probe annealing mechanism. Single molecules are deposited on the surface as before with a cleavable linker on the bead. Following deposition, the bead is cleaved off and a poly-T modified single stranded DNA, is annealed. Sequencing by synthesis of the unknown template may then readily proceed.

DETAILED DESCRIPTION OF THE INVENTION

Figure 2:
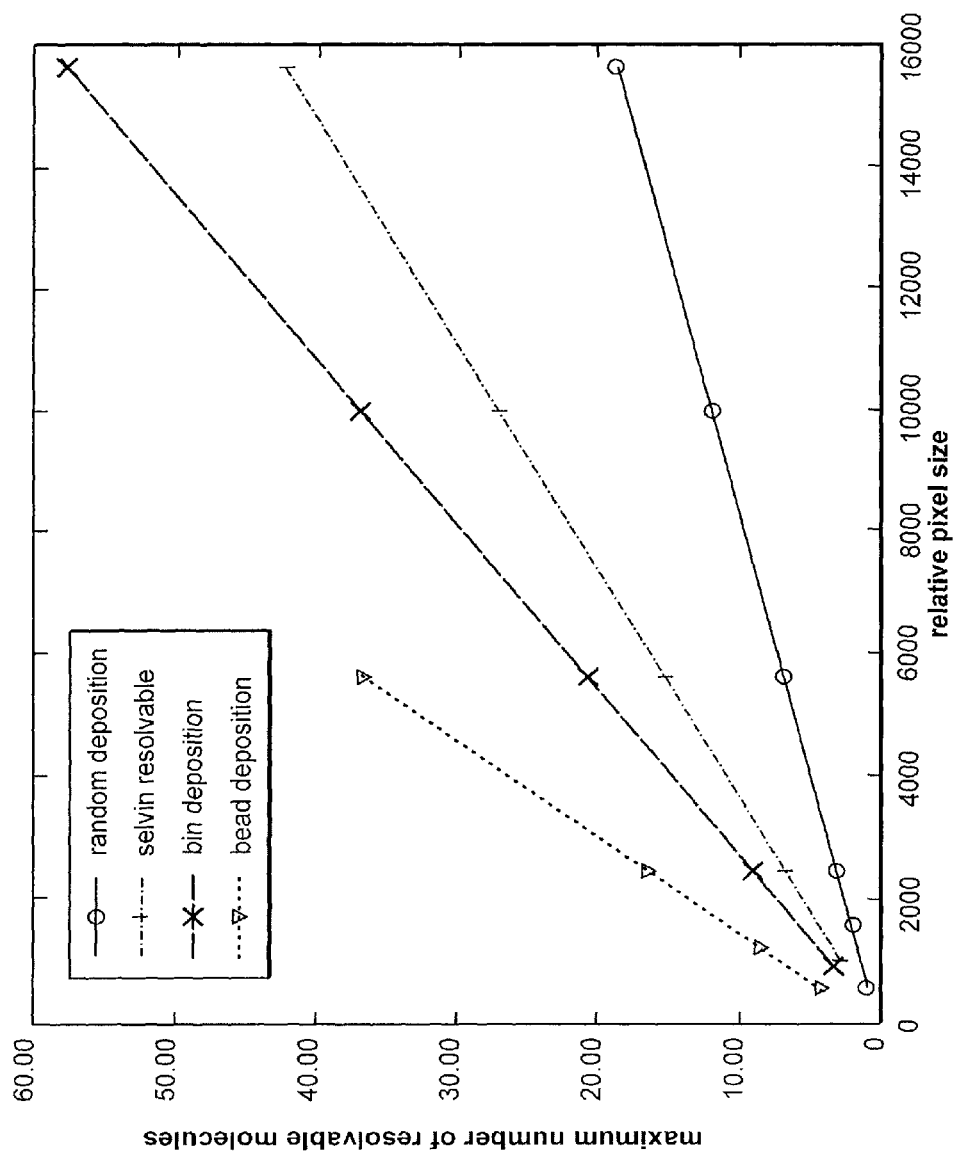
FIG. 2 shows the results of a computer simulation showing the maximum number of resolvable molecules as a function of the diffraction limit and the physical size of the photon detector for a variety of different single molecule deposition methods. 'O'=random deposition method; '+'=random deposition method with Selvin resolution of single molecules; 'x'=bin deposition (see Variations); 'v'=bead deposition. Relative pixel size=(detector length/$d_R$)$^2$

The following detailed description provides various aspects of the invention and a variety of ways in which it can be implemented. However, the following description is not intended to be limiting and is merely exemplary of the full range of application of the invention.

Surface Chemistry Methods & Materials

A thin (1-10 nm) gold film is uniformly deposited on a RCA clean glass coverslip (Schott Glass Technologies, D-263T cut glass, 0.21 mm, 2"×1" 40/20 surface quality). The gold coated coverslip is then washed 5× with Millipore pure water, dried with nitrogen atmosphere, and soaked in a fresh 1 mM ethanolic solution of 11-amino-1-undecanethiol (Dojindo) for 24 hours. The coverslip is extensively washed with ethanol, water, and dried under nitrogen atmosphere. The surface is immediately incubated in a fresh 0.1M solution of sulfo-SMCC (Pierce) in 0.1M triethanolamine, pH 7.0, for 30-45 minutes, with occasional mixing, to create a thiol-reactive surface. Thiol-containing fluorescently labeled biomolecules, such as single or double stranded DNA containing reduced 5', 3', or internal thiol-modifiers, can then be coupled to the surface by incubation at high concentration (500 pM-1 OnM) for 24 hours in 10 mM Tris pH 8.0, 50 mM NaCl buffer. Verification of the surface fabrication procedure is done via x-ray photoelectron spectroscopy (XPS).

The location and intensity of the fluorophores is then identified directly via TIRF with the addition of an oxygen-scavenging solution to reduce photobleaching (4). The oxygen scavenger solution is typically comprised of 0.4% Glucose, 0.1% β-mercaptoethanol, 10 mM MgCl2, 1% Gloxy (Gloxy=1,665 units glucose oxidase, (G-7016, Sigma), ~26000 units Catalase (106810, Roche), in 100 µl T50 buffer, filtered with 0.2 µm syringe filters and centrifuged for 5 minutes at 13,000 g}, in 10 mM Tris pH 8.0, 50 mM NaCl buffer.

Deposition Methods & Materials

A glass coverslip (Schott Glass Technologies, D-263T cut glass, 0.21 mm, 2"×1" 40/20 surface quality) is RCA cleaned and a polyelectrolyte multilayer comprised of alternating layers of polyethylenimine (Sigma) and polyacrylic acid (Sigma) is deposited. The coverslips are immersed in a 2 mg/mL solution of polyethyleneimine for 10 minutes, washed extensively with Millipore pure water, then immersed in a 2 mg/mL solution of polyacrylic acid for 10 minutes followed by extensive MP water washing. This process is repeated four to seven more times to yield a uniform negatively charged surface with an increase in charge density with each absorbed layer. The terminal polyacrylic acid surface is then functionalized with biotin (Pierce, EZ-Link Biotin-PEO-LC-amine) through a 1-ethyl-3(3 dimethylaminopropyl)-carbodiimide (EDC, Sigma) activated reaction by surface incubation of 0.96 mg/mL EDC with 2.1 mg/mL biotin in 0.1 M i2-(N-morpholino)ethanesulfonic acid] (MES), 0.9 NaCl, pH 4.7 (Pierce) for 10 minutes. The biotinylated surface is then incubated for 20 minutes with 0.1 mg/mL neutravidin (Pierce) in 0.01% sodium azide, 10 mM Tris, 50 mM NaCl. A bis-biotinylated double stranded DNA construct covalently attached to a bead is then attached to the surface neutravidin monolayer as described below.

The bead-DNA construct may be made as follows: 300 nm diameter amine-functionalized silica beads (Corpuscular) are made thiol-reactive through incubation with sulfo-SMCC (Pierce) at 100-fold SSMCC concentration over the surface amine group concentration in 20 mM HEPES at pH 7.5 for 1 hour on a shaker at room temperature. The beads are then thoroughly washed at 4 C. with ice-cold 1 mM MES pH 6.0 to drop the free sulfo-SMCC concentration to below 10 fM. The thiol-reactive beads are then covalently coupled to biotinylated and fluorescently labeled double stranded DNA containing a reduced 5' or 3' thiol modification (Integrated DNA Technologies) to produce the construct shown in FIG. 1. The sequence of the dsDNA ideally contains a Type II or Type Ifs restriction enzyme cut site to allow for cleavage and removal of the bead and fluorophore. The biotinylated DNA construct is then incubated with the neutravidin-coated surface for 20 minutes at room temperature and excess DNA is removed by extensive washing with Millipore water.

Surface Chemistry

The general surface attachment method described above measures changes in the refractive index of solutions in contact with the surface, typically as a result of ligand binding. Here, we use a thinner metal film so that we can use TIRF microscopy to take optical images of fluorescent molecules on the solution side of the film.

The invention allows real time imaging of single fluorophores on molecules using a substrate-specific attachment chemistry to a thin metal film using surface plasmon resonance ("SPR") fluorescence microscopy.

Surface Deposition Methods

When a single biotinylated DNA-bead construct is coupled to a neutravidin surface, the negative electrostatic interactions between the polyelectrolyte multilayer and the rigid DNA backbone (persistence length=50 nm) help to ensure that the construct remains normal to the surface. In addition, the presence of the silica bead on the distal end of the construct will sterically hinder any other constructs from coupling within a diameter radius.

If the bead diameter is chosen while taking into account the fluorophore being imaged, every molecule deposited on the surface can be placed at least a diffraction limit away from every other molecule. Provided that the relative pixel size in the optical setup is sufficiently smaller than the diffraction limit required to be able to differentiate between two adjacent single molecules (eg. one pixel width corresponds to less than $0.61\lambda/N.A.$ nm), this will allow every deposited single molecule to be resolved.

The Type II or Type IIs restriction enzyme site shown in FIG. 1 allows selective DNA cleavage such that both the bead and a cy3-fluorophore can be washed away from the surface. This feature will allow quantitative assessment of the efficiency of the cleavage and will reduce background fluorescence during future imaging measurements. If the site is chosen such that after cleavage a 5' overhang remains, direct single base extension experiments may be done for sequencing or genotyping purposes. Alternatively, external probe DNA fragments with appropriate sticky ends may be annealed to the overhang for the sequencing or genotyping an unknown template.

Computer simulations were done to determine the theoretical effectiveness of this method at improving the total number of resolvable molecules over previous methods. As illustrated in FIG. 2, the bead deposition method described here offers at least a 7-fold increase in the maximum number of resolvable molecules over completely random deposition. For comparison, we also show the maximum number of resolvable molecules obtainable using a bin deposition method and using an a posteriori photobleaching analysis method to resolve two single molecules within a diffraction-limited area (labeled 'Selvin' in FIG. 2).

The invention provides single molecule surface deposition techniques that actively force molecules to be deposited at least a diffraction limit away from each other. By enforcing diffraction limit spacing during a random molecule surface deposition, we improve the total maximum number of resolvable molecules for a given surface by a factor of 7-fold over unregulated random deposition.

In addition to attaining a higher specific density, metal-coated surfaces effectively combine the sensitivity and detection limits of TIR fluorescence microscopy with the enhanced evanescent wave and surface plasmon quenching effects produced via SPR. This is accomplished in conjunction with a surface attachment chemistry that is specific for only certain labeled biomolecules, which will prove to be extremely useful for many biological applications.

For SPR-enhanced TIRF imaging, the type of the metal film may be varied to include metals such as gold, silver, aluminum, chrome, and platinum. The film may also be comprised of multiple layers of different material that vary in thickness. The chemical method of linking target biomolecules to the surface may also be modified to accommodate different types of metals, variations in working distance, and different target functional groups.

The bead-based diffraction limit spacing deposition method may also be selectively modified for specific applications. For example, the sequence of the template, the functional group for surface attachment, or the bead-DNA coupling chemistry may be modified to optimize certain applications. A deposited bead-labeled poly-$(A)_{50}$ single strand of DNA, with a selectively cleavable bead-DNA linker, could be used as a universal attachment probe for poly-$(T)_{50}$ modified single stranded DNA. Such a linker may conceivably be susceptible to cleavage by light absorption, acid or alkaline hydrolysis, or reducing conditions. If the poly-$(T)_{50}$ modified single stranded DNA is generated from short (100 bp) random fragments derived from genomic DNA and annealed to the surface, this could create an extremely high density array of completely resolvable single DNA molecules that are pre-primed for shotgun DNA sequencing (FIG. 3).

Another variation would be to generate the poly-$(T)_{50}$ modified single stranded DNA from expressed sequence tags (ESTs) from a certain organism and anneal them to the poly-$(A)_{50}$ surface. Once the array is decoded, this platform would be the first completely resolvable single molecule microarray for gene expression analysis. Further modification of this scheme is clearly possible.

A more general approach is to create an surface pattern comprised of ordered reactive features with diffraction limit spacing. A bin could conceivably be any isolated specific surface attachment feature such as a circular spot of gold or a spot of surface-bound streptavidin. The width of the Gaussian point spread function for excited fluorophores immobilized within the bin should not significantly overlap with that of neighboring bins. Patterning bins on a surface should be a relatively straightforward process using standard microcontact printing, electron beam lithography, or photolithography methods. Ideally the size of a single bin would be created sufficiently small (on the order of tens of nm) such that, at most, only a handful of molecules are capable of being deposited in a single bin. Fluorescently labeled single molecules are free to be deposited in any bin but are only resolvable if the bin contains a single occupant, and thus the concentration of the molecule to be deposited would be tuned to maximize the number of bins containing a single molecule. Computer simulations of this model, Illustrated in FIG. 2, suggest that it offers an approximately 3-fold increase in the maximum number of resolvable molecules over the random deposition method.

A variation on this invention is to use a specifically designed virus capsid to serve as both the coupling agent between the surface and the dsDNA and as the diffraction limit spacer. For example, a virus capsid containing no cysteine side chains (such as Cowpea Mosaic Virus) with a unique asymmetric unit could be genetically engineered to display a single cysteine residue on its coat. It has previously been shown that CMV containing multiple cysteine residues is capable of being assembled into nanoarrays on a thiol-reactive surface using dip-pen nanolithography for SPR or AFM imaging. As stated previously, diffraction limit spaced surface patterns of circular gold features (with diameters on the order of the virus capsid's diameter), fabricated through standard microcontact printing, electron beam lithography, or photolithography methods, could then be used as a thiol-reactive surface such that only a single capsid is capable of coupling to a single feature. Similar work has previously been done to generate ordered patterning of cells on self assembled monolayers of alkane thiolates on gold. The present method creates an ordered array of specifically hound virus capsids capable of being completely optically resolved. It is straightforward to couple a single fluorescently labeled DNA molecule to each capsid using conventional biochemical methods.

The invention claimed is:

1. A method for single molecule visualization, the method comprising:
providing a surface, wherein the surface is a glass surface further comprising a uniform metal film, and wherein the surface is produced by a method comprising depositing a plurality of surface attachment features for specifically immobilizing fluorophore-labeled molecules on said surface by a deposition method that actively forces individual fluorophore-labeled molecules to be spaced apart by a distance equal to at least the diffraction limit for said fluorophore, wherein the deposition method provides at least a 3-fold increase in the maximum number of resolvable fluorophore-labeled molecules, as compared to random deposition;
immobilizing a plurality of fluorophore-labeled molecules via the plurality of surface attachment features; and
performing real time imaging for single fluorophores using surface plasmon resonance (SPR) fluorescence microscopy.

2. The method of claim 1, wherein said performing real time imaging comprises:
producing an evanescent electromagnetic field on said surface; and
visualizing said fluorophore-labeled molecules using surface plasmon resonance-enhanced total internal reflection fluorescence microscopy.

3. The method of claim 1, wherein said plurality of surface attachment features comprises a nucleic acid.

4. The method of claim 3, wherein said nucleic acid is DNA.

5. The method of claim 3, further comprising obtaining a sequence of said nucleic acid.

6. The method of claim 5, wherein said obtaining step comprises conducting a template-dependent sequencing-by-synthesis reaction.

7. The method of claim 1, wherein said surface further comprises a coating selected from a polyelectrolyte multilayer and an epoxide.

8. The method of claim 1, wherein the deposition method provides at least a 7-fold increase in the maximum number of resolvable fluorophore-labeled molecules, as compared to random deposition.

9. The method of claim 1, wherein the deposition method comprises the use of a diffraction limit spacer that produces a diffraction limit spacing by sterically hindering attachment features from depositing within the diffraction limit of a given deposited attachment feature.

10. The method of claim 9, wherein the diffraction limit spacer comprises a bead.

11. The method of claim 9, wherein the diffraction limit spacer comprises a virus or virus capsid.

12. The method of claim 1, wherein the metal film is 1-10 nm thick.

13. The method of claim 1, wherein said depositing a plurality of surface attachment features comprises creating a surface pattern of ordered surface attachment features with diffraction limit spacing, wherein each surface attachment feature comprises a bin, whereby a single fluorophore-labeled molecule immobilized at said bin is optically resolvable from fluorophore-labeled molecules immobilized at other bins.

14. The method of claim 13, wherein said depositing of surface attachment features is carried out by microcontact printing, electron beam lithography, or photolithography.

15. The method of claim 1, wherein said plurality of attachment features is selected from antibodies, ligands, gold particles, beads, wells, surface dimples, amines, and epoxides.

16. The method of claim 1, wherein the method comprises sequencing a nucleic acid, wherein:

said immobilizing a plurality of fluorophore-labeled molecules comprises:
   attaching a plurality of nucleic acid primers to the plurality of surface attachment features;
   exposing said primers to one or more template nucleic acids that are capable of hybridizing thereto;
   introducing a fluorophore-labeled nucleotide and a polymerase under conditions that permit template-dependent incorporation of said nucleotide into said primer;
said performing real time imaging comprises:
   detecting said incorporated nucleotides; and
the method additionally comprises:
   neutralizing fluorophores associated with said incorporated nucleotides; and
   repeating said introducing, detecting, and neutralizing steps at least once, thereby to determine a sequence of said template.

* * * * *

SEQUENCE LISTING

```
<160> NUMBER OF SEQ ID NOS: 5

<210> SEQ ID NO 1
<211> LENGTH: 37
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(37)
<223> OTHER INFORMATION: n is a, c, g, or t
<220> FEATURE:
<221> NAME/KEY: misc_feature
<222> LOCATION: (1)..(1)
<223> OTHER INFORMATION: 5' terminal modified with bis-biotin
<220> FEATURE:
<221> NAME/KEY: misc_feature
<222> LOCATION: (37)..(37)
<223> OTHER INFORMATION: 3' terminal modified with thiol-SMCC-Bead

<400> SEQUENCE: 1
nnnnnnnnnn nnnnnnnnnn nnnnnnnnnn nnnnnnn                              37

<210> SEQ ID NO 2
<211> LENGTH: 37
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(37)
<223> OTHER INFORMATION: n is a, c, g, or t
<220> FEATURE:
<221> NAME/KEY: misc_feature
<222> LOCATION: (1)..(1)
<223> OTHER INFORMATION: 5' terminal modified with Cy3

<400> SEQUENCE: 2
nnnnnnnnnn nnnnnnnnnn nnnnnnnnnn nnnnnnn                              37

<210> SEQ ID NO 3
<211> LENGTH: 70
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5' terminal modified with bis-biotin
<220> FEATURE:
<221> NAME/KEY: misc_feature
<222> LOCATION: (70)..(70)
<223> OTHER INFORMATION: 3' terminal modified with cleavable linker-bead

<400> SEQUENCE: 3
aaaaaaaaaa aaaaaaaaaa aaaaaaaaaa aaaaaaaaaa aaaaaaaaaa aaaaaaaaaa    60
aaaaaaaaaa                                                            70
```

```
<210> SEQ ID NO 4
<211> LENGTH: 70
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5' terminal modified with bio-biotin

<400> SEQUENCE: 4
aaaaaaaaaa aaaaaaaaaa aaaaaaaaaa aaaaaaaaaa aaaaaaaaaa aaaaaaaaaa      60
aaaaaaaaaa                                                              70

<210> SEQ ID NO 5
<211> LENGTH: 91
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(21)
<223> OTHER INFORMATION: n is a, c, g, or t

<400> SEQUENCE: 5
nnnnnnnnnn nnnnnnnnnn nttttttttt tttttttttt tttttttttt tttttttttt      60
tttttttttt tttttttttt tttttttttt t                                      91
```